(12) United States Patent
Collins

(10) Patent No.: US 6,558,336 B2
(45) Date of Patent: May 6, 2003

(54) CONTINUOUS INTRA-CRANIAL PRESSURE CONTROL

(76) Inventor: Ronald Collins, 681 E. 78th St., Apt. 1, Brooklyn, NY (US) 11236

( * ) Notice: Subject to any disclaimer, the term of this patent is extended or adjusted under 35 U.S.C. 154(b) by 41 days.

(21) Appl. No.: 09/879,630

(22) Filed: Jun. 12, 2001

(65) Prior Publication Data
US 2002/0128569 A1 Sep. 12, 2002

Related U.S. Application Data
(60) Provisional application No. 60/210,676, filed on Jun. 10, 2000.

(51) Int. Cl.[7] ................................................. A61B 5/03
(52) U.S. Cl. ........................................ 600/561; 600/301
(58) Field of Search .................................. 600/301, 561

(56) References Cited

U.S. PATENT DOCUMENTS

| 4,688,577 A | * | 8/1987 | Bro .............................. 600/483 |
| 4,723,556 A | * | 2/1988 | Sussman ....................... 600/561 |
| 4,739,771 A | * | 4/1988 | Manwaring ................... 600/504 |
| 4,858,619 A | * | 8/1989 | Toth ............................. 600/561 |
| 5,074,310 A | * | 12/1991 | Mick ............................ 600/561 |
| 5,464,012 A | * | 11/1995 | Falcone ........................ 600/301 |
| 5,579,774 A | * | 12/1996 | Miller et al. ................. 600/479 |
| 5,975,081 A | * | 11/1999 | Hood et al. .................. 128/845 |

* cited by examiner

Primary Examiner—Michael Powell Buiz
Assistant Examiner—Ramesh Krishnamurthy
(74) Attorney, Agent, or Firm—Goldstein & Lavas, P.C

(57) ABSTRACT

An intracranial pressure monitor including a ventilator having an outlet tube coupling with a patient's airway. An arterial line is coupled with an artery of the patient. An intracranial monitor is coupled with a skull of a patient. A monitor is provided that is in communication with the ventilator, the arterial line, and the intracranial monitor. The monitor includes gauges for monitoring carbon dioxide levels in the skull of the patient. The monitor includes an alarm in communication with the gauge for monitoring carbon dioxide levels.

2 Claims, 2 Drawing Sheets

CONTINUOUS INTRA-CRANIAL PRESSURE CONTROL

CROSS REFERENCES AND RELATED SUBJECT MATTER

This application relates to subject matter contained in provisional patent application Ser. No. 60/210,676, filed in the United States Patent Office on Jun. 10, 2000.

BACKGROUND OF THE INVENTION

The present invention relates to an intracranial pressure monitor and more particularly pertains to monitoring the intracranial pressure of a patient who sustained a severe head injury.

Measurement of intracranial pressure has become a routine neurosurgical procedure used in monitoring patients with conditions such as head injury, intracranial infection, hemorrhage, and hydrocephalus. Generally when intracranial pressure reaches 20 mm Hg it becomes a concern and when it reaches 25 mm Hg for more than two minutes it is considered life threatening. When levels of intracranial pressure reach above 25 mm Hg, it is imperative to reduce the partial pressure of carbon dioxide. This is done by increasing the ventilation rate. This is done without reducing the $PCO_2$ to such a level that might cause cerebral vasoconstriction and stroke.

The present invention attempts to solve the abovementioned problem by providing a machine that will monitor the intracranial pressure so as to increase or decrease ventilation and will also vent cerebral spinal fluids as needed, when the monitor is cannulated.

The use of medical devices for measuring pressure is known in the prior art. More specifically, medical devices for measuring pressure heretofore devised and utilized for the purpose of monitoring pressure are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,723,556 to Sussman discloses an intracranial catheter with a pressure gauge for monitoring pressure and appears capable of increasing or decreasing ventricular volume quickly. U.S. Pat. No. 4,114,603 to Wilkinson discloses an intracranial pressure monitoring catheter with means to reduce the possibility of infection. U.S. Pat. No. 5,117,836 to Millar discloses a means for measuring intracranial fluid of the brain with the use of a transducer tipped catheter, but such a monitor cannot vent CSF. U.S. Pat. No. 5,117,835 to Mick discloses a means for measuring changes in intracranial pressure in a patient's skull by monitoring dynamic vibration characteristics. U.S. Pat. No. 5,464,012 to Falcone discloses a patient monitoring system capable of generating an alarm when a measure parameter falls beyond preset limits.

The essential ingredient in carrying out "continuous intracranial pressure control" is to have a $CO_2$ pressure sensor (Piezo Electric) in parallel with a cannulated intracranial pressure monitor. This sensor could be set for keeping the ICP below 25 mm Hg by (1) increasing the artificial ventilation rate, and if this did not suffice, (2) venting CSF until the ICP fell to, or below 25 mm Hg, or if the ICP still did not fall, (3) for it to set off a loud alarm (so that the patient would not suffer a cerebral perfusion deficit.

The $PCO_2$ would also have to be kept from falling below 25 mm Hg when such intense vasoconstriction might cause a stroke in the patient. This "continuous ICP control" by feed-back (Servo-mechanism) is meant to help maintain continuous and necessary brain perfusion in a very vigilant manner, reducing the risk of intermittent low cerebral perfusion insults to the brain.

Basically, Hypocapnia causes the cerebral vessels to vasoconstrict with a 40% decrease in cerebral blood flow (CBF) for every torr change in $PCO_2$ down to 25 torr. Below this level, the vasoconstrictive effect of hypocapnia is diminished or absent. Besides this, there is the danger of stroke secondary to the severe vasoconstriction.

SUMMARY OF THE INVENTION

In the view of the foregoing disadvantages inherent in the known types of medical device for measuring pressure now present in the prior art, the present invention provides an improved continuous ICP control. As such, the general purpose of the present invention, which will be described subsequently in greater detail, is to provide continuous ICP control.

To attain this, the present invention essentially comprises a ventilator having an outlet tube coupling with a patient's airway. An arterial line is coupled with an artery of the brain of the patient. An intracranial monitor is coupled at best with the lateral ventricle. The monitor includes gauges for monitoring carbon dioxide levels in the CSF of the patient. The monitor includes an alarm in communication with the gauge for monitoring carbon dioxide levels.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved intracranial pressure monitor which has all the advantages of the prior art medical device for measuring pressure and none of the disadvantages.

It is another object of the present invention to provide a new and improved intracranial pressure monitor which may be easily and efficiently manufactured and marketed.

It is a further object of the present invention to provide a new and improved intracranial pressure monitor which is of durable and reliable construction.

An even further object of the present invention is to provide a new and improved intracranial pressure monitor which is susceptible of a low cost of manufacture with regard to both materials and labor, and which accordingly is then susceptible of low prices of sale to the consuming public, thereby making such an intracranial pressure monitor economically available to the buying public.

Even still another object of the present invention is to provide a new and improved intracranial pressure monitor for monitoring the intracranial pressure of a patient who sustained a severe head injury.

Lastly, it is an object of the present invention to provide a new and improved intracranial pressure monitoring system including a ventilator having an outlet tube coupling with a patient's airway. An arterial line is coupled with an artery of the patient. An intracranial monitor is coupled with a skull of a patient. A monitor is provided that is in communication with the ventilator, the arterial line, and the intracranial monitor. The monitor includes gauges for monitoring carbon dioxide levels in the skull of the patient. The monitor includes an alarm in communication with the gauge for monitoring carbon dioxide levels.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
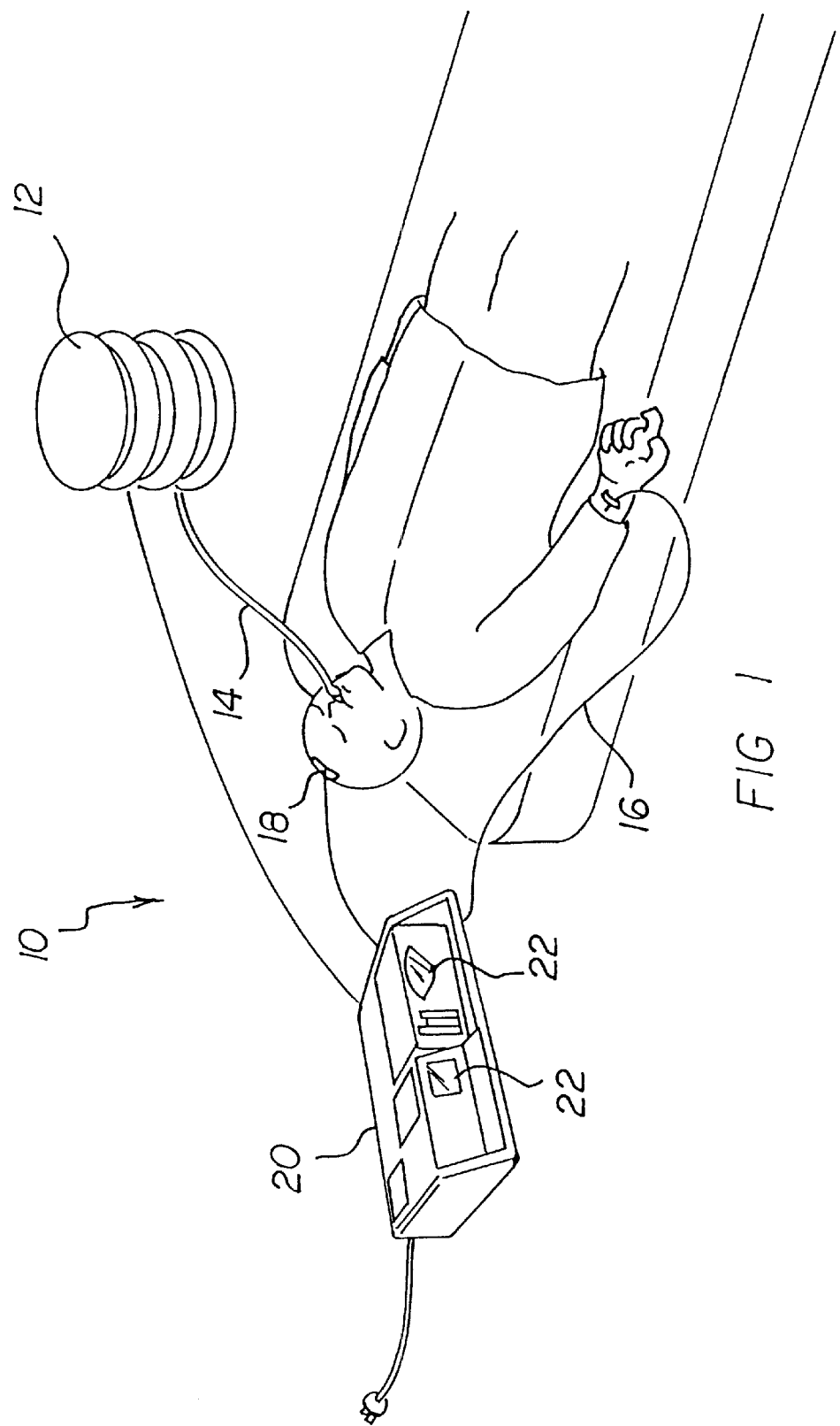
FIG. 1 is a perspective view of the preferred embodiment of the intracranial pressure monitor constructed in accordance with the principles of the present invention.
Figure 2:
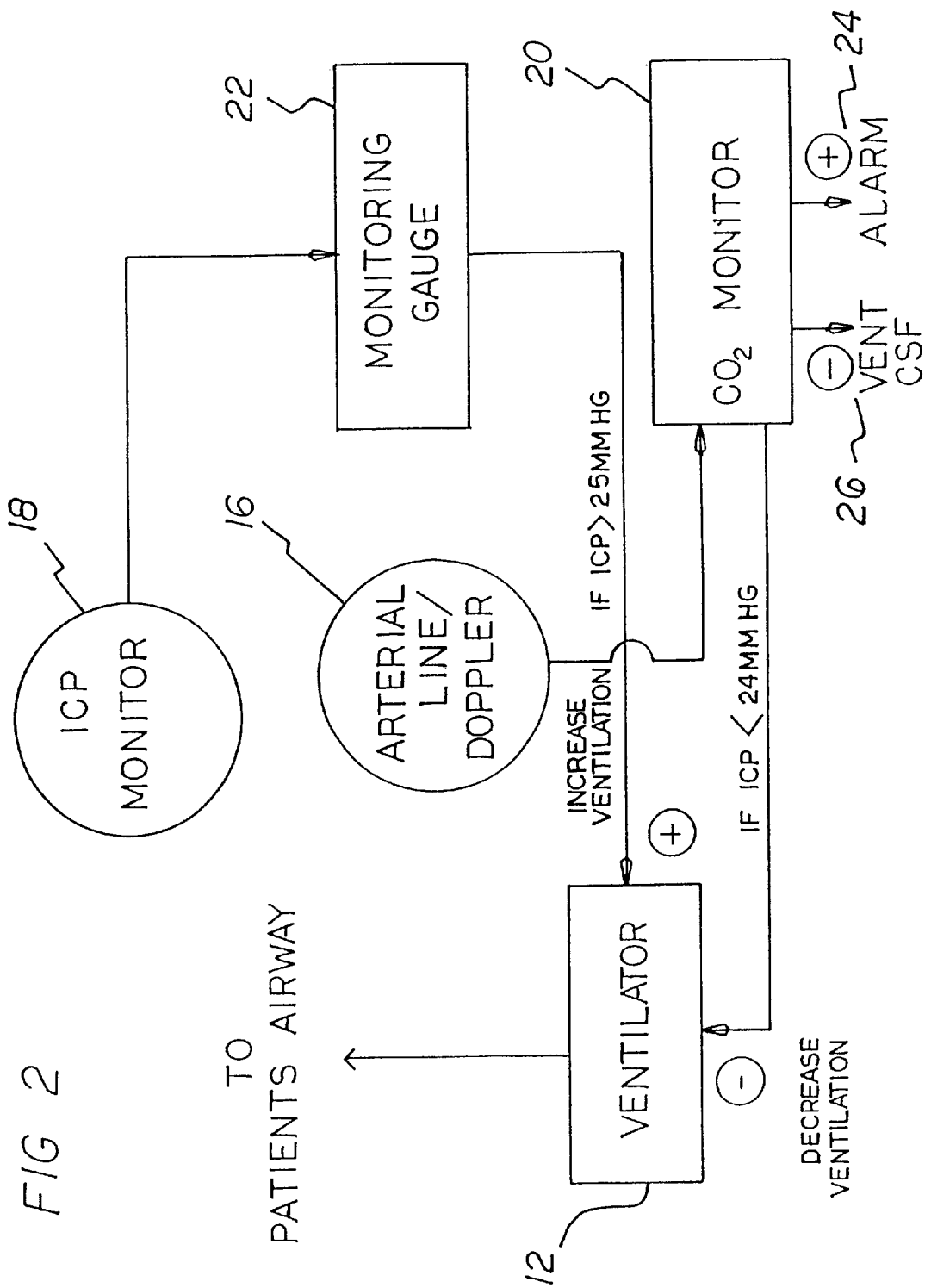
FIG. 2 is a schematic illustration of the present invention.

With reference now to the drawings, and in particular, to FIGS. 1 and 2 thereof, the preferred embodiment of the new and improved intracranial pressure monitor embodying the principles and concepts of the present invention and generally designated by the reference number 10 will be described.

Specifically, it will be noted in the various Figures that the device relates to a intracranial pressure monitor for monitoring the intracranial pressure of a patient who sustained a severe head injury. In its broadest context, the device consists of a ventilator, an arterial line, an intracranial monitor, and a monitor. Such components are individually configured and correlated with respect to each other so as to attain the desired objective.

The ventilator 12 has an outlet tube 14 coupling with a patient's airway. FIG. 1 illustrates the outlet tube 14 extending within the nasal passage of the patient.

The arterial line 16 is coupled with an artery of the patient. FIG. 1 illustrates the arterial line 16 coupling with an artery in the arm of the patient.

The intracranial monitor 18 is coupled with a skull of a patient. The intracranial monitor will serve to track the level of intracranial pressure within the skull of the patient.

The monitor 20 is in communication with the ventilator 12, the arterial line 16, and the intracranial monitor 18. The monitor 20 includes gauges 22 for monitoring carbon dioxide levels in the skull of the patient. The monitor 20 includes an alarm 24 in communication with the gauge 22 for monitoring carbon dioxide levels. Once the level of intracranial pressure falls below 24 mm Hg, the monitor 20 will communicate with a ventilation catheter 26 so as properly adjust a level of cerebral spinal fluid.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. An intracranial pressure monitoring system for monitoring the intracranial pressure of a patient who sustained a severe head injury comprising, in combination:

a ventilator having an outlet tube for coupling with the patient's airway;

an arterial line coupled with an artery of the patient;

an intracranial monitor coupled with a skull of the patient, for tracking the level of intracranial pressure within the skull of the patient;

a monitor in communication with the ventilator, the arterial line, and the intracranial monitor, the monitor activating the ventilator in response to the intracranial pressure detected by the intracranial monitor, the monitor including gauges for monitoring carbon dioxide levels in the skull of the patient, the monitor including an alarm in communication with said gauges for monitoring carbon dioxide levels.

2. The intracranial pressure monitoring system as recited in claim 1, further comprising a ventilation catheter in communication with the monitor, for coupling to the patient and adjusting the level of cerebral spinal fluid in the patient when intracranial pressure drops below 24 millimeters mercury.

* * * * *